(12) United States Patent
Hirasawa et al.

(10) Patent No.: US 7,524,407 B2
(45) Date of Patent: Apr. 28, 2009

(54) GAS SENSOR

(75) Inventors: Makoto Hirasawa, Aichi (JP); Shohei Yoshiyasu, Aichi (JP); Yoshiaki Matsubara, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 742 days.

(21) Appl. No.: 11/092,803

(22) Filed: Mar. 30, 2005

(65) Prior Publication Data
US 2005/0224349 A1    Oct. 13, 2005

(30) Foreign Application Priority Data
Mar. 31, 2004   (JP) ............................. 2004-106905

(51) Int. Cl.
*G01N 27/26* (2006.01)
(52) U.S. Cl. .................. 204/425; 204/421; 204/426; 205/783.5; 205/785; 73/23.31; 73/23.32; 439/33; 439/913
(58) Field of Classification Search ......... 204/421–432; 205/785.5–785; 73/23.31–23.32; 439/33, 439/585, 610
See application file for complete search history.

(56) References Cited

U.S. PATENT DOCUMENTS 5,759,365 A * 6/1998 Yamada et al. ............. 204/424
6,383,353 B1  5/2002 Akatsuka et al.

FOREIGN PATENT DOCUMENTS

JP    2001-66281    3/2001

* cited by examiner

*Primary Examiner*—Bach T Dinh
(74) *Attorney, Agent, or Firm*—Sughrue Mion, PLLC

(57) ABSTRACT

An oxygen sensor 10 includes an oxygen detection element 20, which assumes a hollow tubular shape extending along the axis. The oxygen detection element 20 has a closed tip end and an opened rear end. An internal electrode layer 23 is formed on an inner circumferential surface 22 of the oxygen detection element 20. The sensor 10 also has a terminal member 30 which is in contact with the internal electrode layer 23 and in electrical connection therewith. The terminal member 30 has press contact portions 34c and 34d which come into press contact with the inner circumferential surface 22 of the oxygen detection element 20 to hold the terminal member 30 in the oxygen detection element 20, and conduction portions 35b which come into press contact with the internal electrode layer 23 on the inner circumferential surface 22 of the oxygen detection element 20 and into electrical connection with the internal electrode layer 23. Pressing force per unit area at the conduction portions 35b is smaller than that at the press contact portions 34c and 34d.

13 Claims, 11 Drawing Sheets

Fig.8 (a)          Fig.8 (b)
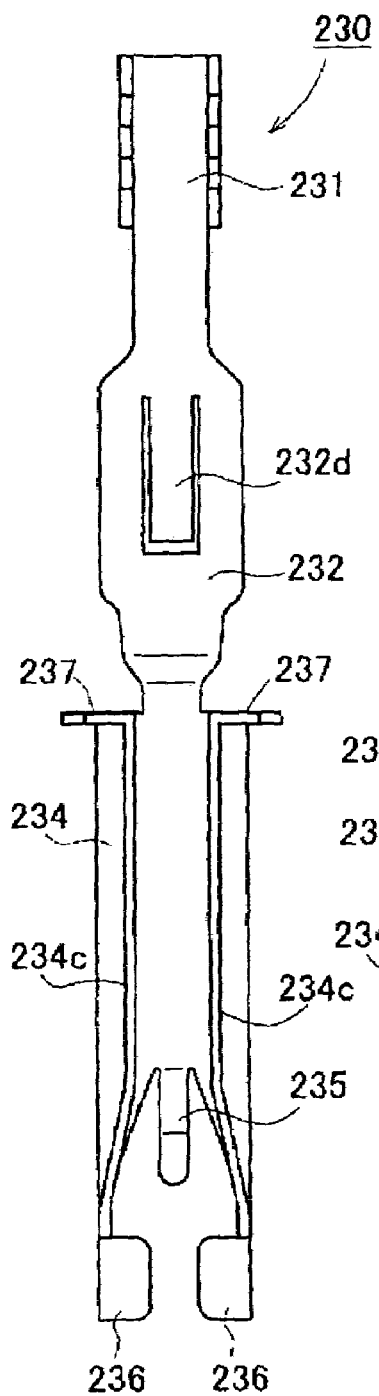
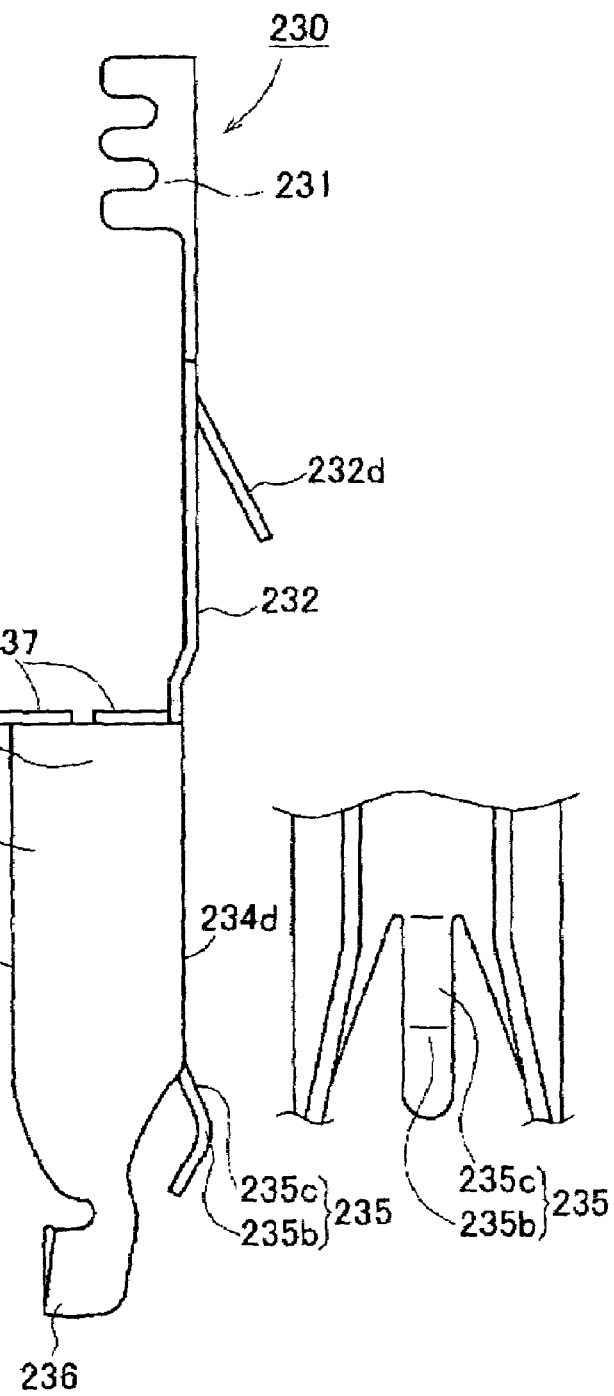

GAS SENSOR

BACKGROUND OF THE INVENTION

1. Field of the Invention

The present invention relates to a gas sensor for detecting the concentration of a gas component contained in a gas to be measured.

2. Description of the Related Art

A specific example of a gas sensor for detecting the concentration of a gas component is the oxygen sensor disclosed in Patent Document 1. The disclosed oxygen sensor has an oxygen detection element which assumes a hollow tubular shape. The oxygen detection element has a closed front end and an opened rear end, and extends along an axial direction. An electrode layer (hereinafter also referred to as an internal electrode layer) is formed on the inner circumferential surface thereof.

In this type of oxygen sensor, while atmospheric air serving as a reference gas is introduced into the oxygen detection element such that the internal electrode layer is exposed to the reference gas, an external electrode layer formed on the outer circumferential surface of the oxygen detection element is exposed to a gas to be measured. As a result, an electromotive force is induced in accordance with the difference in oxygen concentration between the inner and outer circumferential surfaces. This electromotive force, which serves as a signal indicative of the detected oxygen concentration of the measured gas, is led outside the sensor from the internal and external electrode layers via terminal members, lead wires, etc., whereby the oxygen concentration of the measured gas can be detected.

A terminal member for conveying an electromotive force from the internal electrode layer of the oxygen detection element is formed of a member, such as a metallic plate, which has elasticity and electrical conductivity. This terminal member has press contact portions which come into pressure contact with the internal electrode layer of the oxygen detection element to thereby hold the terminal member itself.

Patent Document 1 shows a terminal member having a press contact portion which is formed such that it has a generally horseshoe-shaped radial cross section as viewed in a radial direction perpendicular to the axis thereof and such that, in a free state, the diameter of a circumcircle of the radial cross section (a circle circumscribing the radial cross section) is larger than that of the inner circumferential surface of the oxygen sensor. When the terminal member is assembled into the oxygen detection element, because of elasticity of the terminal member, two tip end portions and a base-side center portion of the terminal member as viewed in the generally horseshoe-shaped radial cross section serve as press contact portions which come into press contact with the inner circumferential surface of the oxygen detection element. By means of the pressing force of the press contact portions, the terminal member is held within the oxygen detection element and is brought into press contact with the internal electrode layer. Simultaneously, electrical continuity is established between the internal electrode layer of the oxygen detection element and the press contact portions, whereby an electromotive force can be conveyed from the internal electrode layer of the oxygen detection element to the outside via the terminal member.

[Patent Document 1] Japanese Patent Application Laid-Open (kokai) No. 2001-66281 (FIGS. 1, 3, and 8)

DISCLOSURE OF THE INVENTION

3. Problems to be Solved by the Invention

However, in order to assemble the terminal member to the interior of the oxygen detection element, the terminal member is slidingly inserted therein in a state in which the press contact portions of the terminal member are pressed against the inner circumferential surface of the oxygen detection element. That is, the contact press portions of the terminal members are press-fitted into the oxygen detection element. During press-fitting, because of friction generated between the press contact portions and the inner circumferential surface of the oxygen detection element, portions of the internal electrode layer in friction contact with the press contact portions may be scraped and become thinner or may exfoliate. Notably, the internal electrode layer is generally formed by plating platinum or other suitable material, and has a small thickness of a few $\mu m$. At the portions where the internal electrode layer has been scraped to become thinner or has exfoliated, the reliability of electrical continuity between the terminal member and the internal electrode layer of the oxygen detection element may be lowered.

One measure for addressing this problem is to reduce the friction force between the press contact portions and the internal electrode layer by lowering the pressing force of the press contact portions of the terminal member, to thereby suppress damage to the internal electrode layer. However, when the pressing force of the press contact portions is reduced, the press contact force between the terminal member and the internal electrode layer decreases, possibly resulting in failure to hold the terminal member within the oxygen detection element with sufficient force.

When the press contact portions of the terminal member are formed to play two roles; i.e., holding the terminal member itself and establishing electrical continuity, selection of a suitable pressing force per unit area becomes difficult in some cases. This is because the strength of the electrode layer must be taken into consideration.

SUMMARY OF THE INVENTION

The present invention has been accomplished in view of the above problems. It is therefore an object of the present invention to provide a highly reliable gas sensor in which a terminal member can be held in a gas detection element with a suitable pressing force and good electrical continuity can be established between an internal electrode layer of the gas detection element and the terminal member.

The above object has been achieved by providing a gas sensor comprising a gas detection element which assumes the form of a hollow tube having a closed tip end and an opened rear end and extending along an axis and which has an electrode layer formed on at least a portion of an inner circumferential surface of the gas detection element; and a terminal member which comes into contact with the electrode layer and into electrical connection therewith. The terminal member has a press contact portion which comes into press contact with the inner circumferential surface of the gas detection element to hold the terminal member itself in the gas detection element, and a conduction portion which comes into press contact with the electrode layer on the inner circumferential surface of the gas detection element and into electrical connection with the electrode layer. Furthermore, the pressing force per unit area at the conduction portion is smaller than the pressing force per unit area at the press contact portion.

In the gas sensor of the present invention, a press contact portion for holding the terminal member itself in contact with the inner circumferential surface of the gas detection element, and a conduction portion for establishing electrical connection between the terminal member and the electrode layer, are separately provided on the terminal member. Therefore, at the press contact portion, the terminal member can come into press contact with the inner circumferential surface of the gas detection element with a relatively large pressing force per unit area suitable for holding the terminal member. Meanwhile, at the conduction portion, the terminal member can come into press contact with the electrode layer with a relatively small pressing force per unit area which is determined in consideration of the strength of the electrode layer and is suitable for establishing electrical connection between the terminal member and the electrode layer. Accordingly, since press contact for, holding and press contact for electrical continuity are properly attained, a gas sensor can be obtained which has high reliability in terms of not only holding the terminal member but also establishing electrical continuity.

Notably, the press contact portion of the terminal member of the present invention need not come into contact with the electrode layer, insofar as it comes into press contact with the inner circumferential surface of the gas detection element to thereby hold the terminal member in the gas detection element. Accordingly, the press contact portion may be formed of an insulative material or a metallic member covered with an insulating layer.

The electrode layer on the inner circumferential surface of the gas sensor element has a portion which functions as an electrode for gas detection and a portion which comes into contact with at least the conduction portion of the terminal member. For example, when the electrode layer is formed of an expensive material such as Pt, forming the electrode layer in a minimum necessary region of the gas detection element reduces the amount of the material used. Accordingly, the gas sensor can be made inexpensive.

Examples of the gas sensor include an oxygen sensor, an NOx sensor, and a CO sensor.

In the gas sensor of the present invention, the terminal member not only may have the function of establishing electrical continuity with the electrode layer at the conduction portion, but also the function of holding a heater disposed within the gas detection element or maintaining the posture of the heater.

In the gas sensor described above, preferably, the conduction portion of the terminal member comes into contact with the electrode layer and into electrical connection therewith in a region of the inner circumferential surface of the gas detection element other than a press contact region where the press contact portion is in press contact with the inner circumferential surface and other than a press-contact-portion sliding region, which sliding region is located on a rear end side of the press contact region and in which the press contact portion has slid.

When the terminal member is assembled into the gas detection element, in many cases, the terminal member is inserted into the gas detection element by sliding the terminal member along the direction of the axis in a state in which the press contact portion of the terminal member is in press contact with the inner circumferential surface of the gas detection element. In the case where assembly is performed in such manner, as a result of inserting the terminal member, the press contact portion of the terminal member slides on the inner circumferential surface of the gas detection element while being pressed against the inner circumferential surface. Therefore, if the electrode layer is present on the locus, in the region which the press contact portion has passed, the electrode layer may be scraped or exfoliated.

In contrast, in the gas sensor of the present invention, when the terminal member is inserted into the gas detection element, the conduction portion comes into contact with the electrode layer in a region of the inner circumferential surface of the gas detection element other than the press contact region and the press-contact-portion sliding region; i.e., in a region which the press contact portion of the terminal member has not passed and in which the electrode layer has not been scraped or exfoliated by the press contact portion. Accordingly, reliable electrical continuity can be established between the conduction portion and the electrode layer, whereby a highly reliably sensor can be obtained.

Notably, in the case where the press contact portion has an axially extending form, the press contact region and the press-contact-portion sliding region may overlap partially or completely.

In the gas sensor described above, preferably, the press contact portion also comes into contact with the electrode layer and into electrical connection therewith.

Even when the electrode layer is scraped because of passage of the contact portion of the terminal member, the electrode layer is not necessarily removed completely, and in some cases, the electrode layer partially remains despite a decrease in its thickness. When the press contact portion is caused to come into contact with the electrode layer as in the case of the gas sensor of the present invention, electrical continuity can be established more reliably, whereby the reliability of the gas sensor can be improved further.

In the gas sensor described above, preferably, the terminal member has a tip-end-side continuous portion which extends from the conduction portion toward the tip end side without coming into contact with the inner circumferential surface of the gas sensor element, wherein the tip-end-side continuous portion presses the conduction portion toward the inner circumferential surface of the gas detection element by means of elastic deformation of the tip-end-side continuous portion.

This case assumes that the terminal member has a continuous portion (rear-end-side continuous portion) extending from the conduction portion toward the rear end side. In such case, when the terminal member is inserted into the rear end opening of the gas detection element, the conduction portion is first inserted, and the rear-end-side continuous portion is then inserted. Accordingly, if the conduction portion is brought into press contact with the inner circumferential surface of the gas detection element, friction generated because of the press contact serves as resistance against insertion of the conduction portion. In such case, the conduction portion is not correctly inserted along the axis, whereby a positional shift or deformation may occur.

In contrast, in the gas sensor of the present invention, the terminal member has a tip-end-side continuous portion provided on the tip end side of the conduction portion such that the tip-end-side continuous portion does not come into contact with the inner circumferential surface of the gas sensor element, and the conduction portion extends from the tip-end-side continuous portion. Accordingly, when the terminal member is inserted into the rear end opening of the gas detection element, prior to the conduction portion, the tip-end-side continuous portion enters the gas detection element without coming into contact with the inner circumferential surface of the gas sensor element. After that, the conduction portion is inserted into the gas detection element while being guided by the tip-end-side continuous portion. Therefore, the conduction portion can be smoothly inserted to a correct position on the rear end side of the tip-end-side continuous portion.

Accordingly, the oxygen sensor can be manufactured such that the conduction portion is disposed at a correctly aligned position and presses the inner circumferential surface of the gas detection element with a suitable pressing force per unit area.

In the gas sensor described in any one of the above embodiments, preferably, the terminal portion has a tip-end-side continuous portion which extends from the conduction portion toward the tip end side without coming into contact with the inner circumferential surface of the gas sensor element, and a rear-end-side continuous portion which extends from the conduction portion toward the rear end side without coming into contact with the inner circumferential surface of the gas sensor element, wherein the tip-end-side continuous portion and the rear-end-side continuous portion press the conduction portion toward the inner circumferential surface of the gas detection element by means of elastic deformations of the tip-end-side continuous portion and the rear-end-side continuous portion.

In the gas sensor of the present invention, the terminal member has a tip-end-side continuous portion on the tip end side of the conduction portion. The tip-end-side continuous portion is separated from the inner circumferential surface of the gas detection sensor and continuously extends from the conduction portion. Accordingly, when the terminal member is inserted into the rear end opening of the gas detection element, prior to the conduction portion, the tip-end-side continuous portion enters the gas detection element. After that, the conduction portion is inserted into the gas detection element while being guided by the tip-end-side continuous portion. Therefore, the conduction portion can be smoothly inserted to a correct position on the rear end side of the tip-end-side continuous portion. Accordingly, the oxygen sensor can be manufactured such that the conduction portion is disposed at a correctly aligned position and presses the inner circumferential surface of the gas detection element with a suitable pressing force per unit area.

Further, in the gas sensor of the present invention, the terminal portion has the rear-end-side continuous portion as well. Therefore, the range of adjustment of pressing force of the conduction portion can be widened as compared with terminal members which do not have a rear-end-side continuous portion, whereby adjustment is facilitated. Furthermore, in this gas sensor, since the terminal member has both the tip-end-side continuous portion and the rear-end-side continuous portion continuous with the conduction portion, resonance is less likely to occur as compared with the case where only one of the tip-end-side continuous portion and the rear-end-side continuous portion is formed to extend from the conduction portion. Accordingly, since pressing force is less likely to change because of vibration, the gas sensor has higher reliability in terms of electrical continuity under vibration.

BRIEF DESCRIPTION OF THE DRAWINGS

FIGS. 3(a) and 3(b) are explanatory views showing the entire terminal member according to the first embodiment, wherein FIG. 3(a) is a front view, and FIG. 3(b) is a side view including an enlarged view of a contact portion.

FIGS. 5(a) and FIG. 5(b) are explanatory views showing the state in which the terminal member according to the first embodiment is assembled into the oxygen detection element, wherein FIG. 5(a) is a perpendicular cross section, and FIG. 5(b) is a perspective through-view.

FIGS. 7(a) and 7(b) are explanatory views showing the entire terminal member according to a first modification, wherein FIG. 7(a) is a front view, FIG. 7(b) is a side view including an enlarged view of a contact portion.

FIGS. 8(a) and (b) are explanatory views showing the entire terminal member according to a second modification, wherein FIG. 8(a) is a front view, FIG. 8(b) is a side view including an enlarged view of a contact portion.

FIGS. 9(a) and 9(b) are explanatory views showing the entire terminal member according to a third modification, wherein FIG. 9(a) is a front view, FIG. 9(b) is a side view including an enlarged view of a contact portion.

FIGS. 10(a) and 10(b) are explanatory views showing the entire terminal member according to a second embodiment, wherein FIG. 10(a) is a front view, FIG. 10(b) is a side view including an enlarged view of a contact portion.

FIGS. 11(a) and 11(b) are explanatory views showing the entire terminal member according to a fourth modification, wherein FIG. 11(a) is a front view, FIG. 11(b) is a side view including an enlarged view of a contact portion.

DESCRIPTION OF REFERENCE NUMERALS

Figure 1:
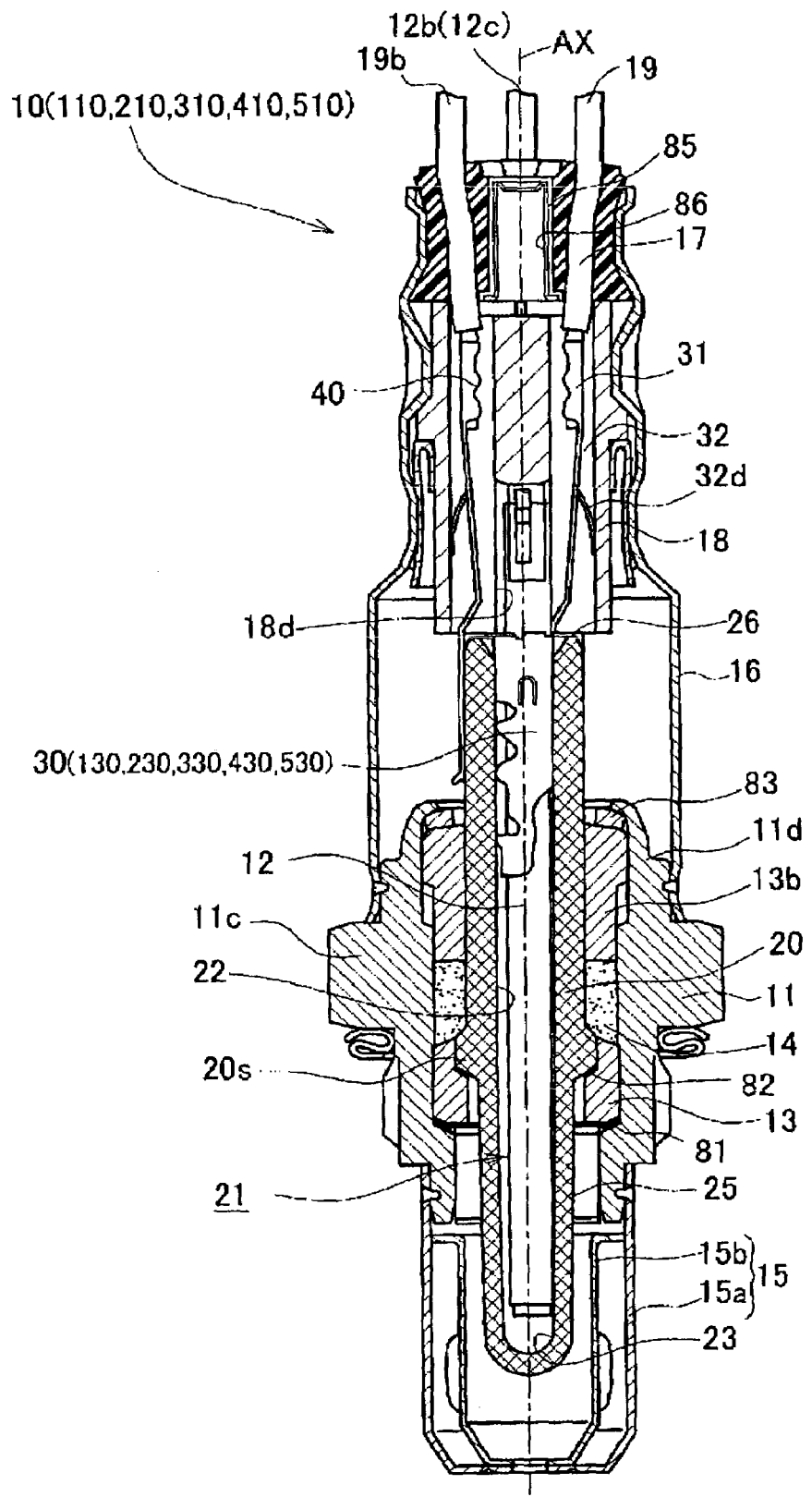
FIG. 1 is a vertical cross sectional view showing the entirety of an oxygen sensor according to a first embodiment.

Reference numbers used to identify various structural features in the drawings include the following.
10, 110, 210, 310, 410, 510: oxygen sensor (gas sensor)
AX: axis (of the oxygen sensor)
12: heater
20: oxygen detection element (gas detection element)
21: bottomed hole (of the oxygen detection element)
22: inner circumferential surface (of the oxygen detection element)
22b: press contact region
22c: press-contact-portion sliding region
23: internal electrode layer (electrode layer on the inner circumferential surface)
24: outer circumferential surface
25: external electrode layer
30, 130, 230, 330, 430, 530: terminal member
31, 131, 231, 331, 431, 531: connector portion
32, 132, 232, 332, 432, 532: separator insertion portion
32d, 132d, 232d, 332d, 432d, 532d: separator engagement portion
33, 133, 233, 333, 433, 533: insertion portion
34, 134, 234, 334, 434, 534: insertion body portion (of the terminal member)
34c, 134c, 234c, 334c, 434c, 534c: end press contact portion (press contact portion)
34d, 134d, 234d, 334d, 434d, 534d: central press contact portion (press contact portion)
35, 1351, 1352, 235, 335, 435, 535: contact portion (of the terminal member)
35b, 1351b, 1352b, 235b, 335b, 435b, 535b: conduction portion 35c, 1351c, 1352c, 435c, 535c: tip-end-side continuous portion
235c, 335c: continuous portion
435d, 535d: rear-end-side continuous portion
N1, N101, N401, N402, N501, N502: punched opening
36, 136, 236, 336, 436, 536: heater pressing portion
37, 137, 237, 337, 437, 537: flange portion

DESCRIPTION OF THE PREFERRED EMBODIMENTS

Oxygen sensors according to the present invention will be described with reference to FIGS. 1 to 11. However, the present invention should not be construed as being limited thereto.

First Embodiment

Figure 2:
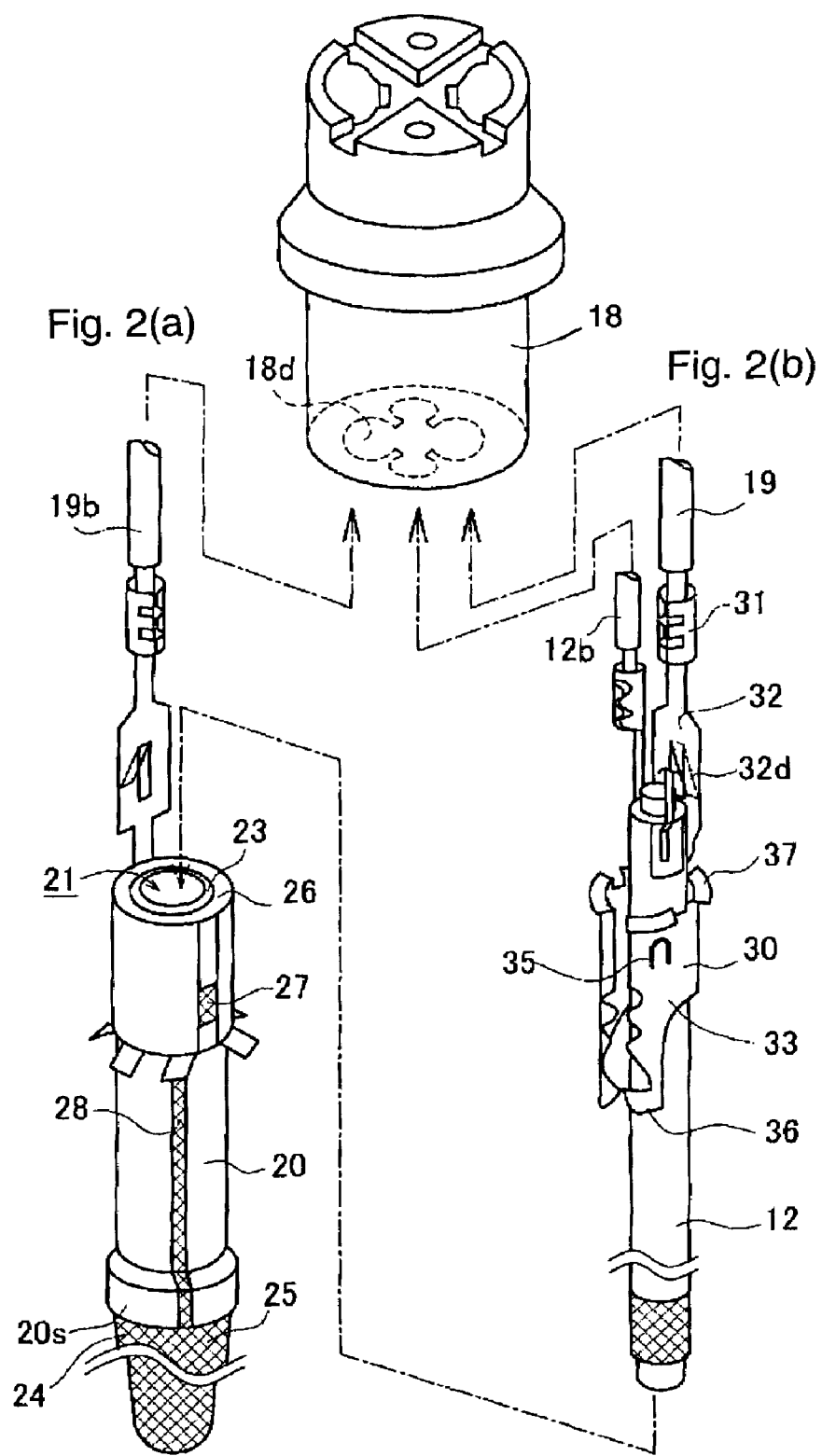
FIGS. 2(a) and 2(b) are exploded perspective views showing assembly of a terminal member and a heater (FIG. 2(b)) into an oxygen detection element (FIG. 2(a)) according to the first embodiment.
FIG. 2(c) is an exploded perspective view of a separator for receiving output lead wires and heater lead wires from the oxygen detection element and heater, respectively.

FIGS. 1 and 2 are vertical and exploded perspective views of an oxygen sensor 10 according to a first embodiment, which show the internal structure thereof. The oxygen sensor 10 includes an oxygen detection element 20 and a metallic shell 11. The oxygen detection element 20 assumes a hollow tubular shape. The oxygen detection element 20 has a closed tip end (a lower end in FIG. 1) and an opened rear end (an upper end in FIG. 1), and extends along the direction of an axis AX (the vertical direction in FIG. 1). The metallic shell 11 has a tubular shape and circumferentially surrounds the oxygen detection element 20. Further, the oxygen sensor 10 has a terminal member 30, a portion of which is inserted into and held in a bottomed hole 21 of the oxygen detection element 20; and a heater 12, which is disposed within the bottomed hole 21 and held by means of the terminal member 30, so that its posture is maintained.

The oxygen detection element 20 is formed of solid electrolyte having oxygen-ion conductivity. A porous internal electrode layer 23 is formed on a circumferential wall of the bottomed hole 21; i.e., an inner circumferential surface 22 of the oxygen detection element 20, so as to cover the entire inner circumferential surface 22. The internal electrode layer 23 is formed of Pt or a Pt alloy by means of known electroless plating. Meanwhile, similarly, a porous external electrode layer 25 is formed on an outer circumferential surface 24 of the oxygen detection element 20 so as to cover the entire region extending toward the front end side from an engagement flange portion 20s, which will be described below (see FIG. 2).

Moreover, as shown in FIG. 2(a), a terminal connection portion 27, which serves as an external-side output extracting portion, is formed in the shape of a strip extending in the circumferential direction, at the rear end side of the outer circumferential surface 24 of the oxygen detection element 20. This terminal connection portion 27 is electrically connected to the external electrode layer 25 via a straight connection lead portion 28. Notably, although not illustrated in FIGS. 1 and 2(a), an electrode protection layer of a porous ceramic is formed on the external electrode layer 25 so as to protect the external electrode layer 25 from poisoning substances such as lead, phosphorous, and silicon, which are contained in a gas to be measured (exhaust gas).

The engagement flange portion 20s, which projects radially outward, is provided at an axially intermediate portion of the oxygen detection element 20. The metallic shell 11 receives and holds the engagement flange portion 20s via metal packings 81, 82, and 83, insulators 13 and 13b, and ceramic powder 14. Thus, the oxygen detection element 20 is held in an airtight manner at the center of the metallic shell 11.

A protector 15 is attached to the metallic shell 11 so as to cover a tip end portion of the oxygen detection element 20 projecting from a tip-end-side opening portion of the metallic shell 11. This protector 15 has an outer protector 15a and an inner protector 15b; i.e., has a double structure. A plurality of gas passage openings for allowing passage of exhaust gas are formed in the outer protector 15a and the inner protector 15b. Accordingly, the external electrode layer 25 of the oxygen detection element 20 is exposed to exhaust gas via the gas passage openings of the protector 15.

Meanwhile, a tip end portion of a tubular metal sleeve 16 is fitted to a connection portion 11d of the metallic shell 11, the connection portion 11d being located on the rear end side of a hexagonal portion 11c of the metallic shell 11. The tip end portion of the tubular metal sleeve 16 is laser-welded to the connection portion 11d over the entire circumference, through external application of a laser beam. A grommet 17 formed of fluorine rubber is fitted into a rear-end-side opening portion of the metal sleeve 16, which is then crimped for sealing. As shown in FIGS. 1 and 2(c), a separator 18 formed of insulative alumina ceramic is provided on the tip-end-side of the grommet 17. Sensor output lead wires 19 and 19b and heater lead wires 12b and 12c extend through the grommet 17 and the separator 18 (see FIG. 1 and FIGS. 2(a), 2(b) and 2(c)).

Notably, a through hole extending along the axis AX is formed at the center of the grommet 17. A metal pipe 86 covered with a sheet filter 85 exhibiting water repellency and air permeability is fitted into the through hole. By virtue of this structure, the atmospheric air outside the oxygen sensor 10 is introduced into the interior of the metal sleeve 16 via the filter 85, and is then introduced into the bottomed hole 21 of the oxygen detection element 20.

Figure 3:
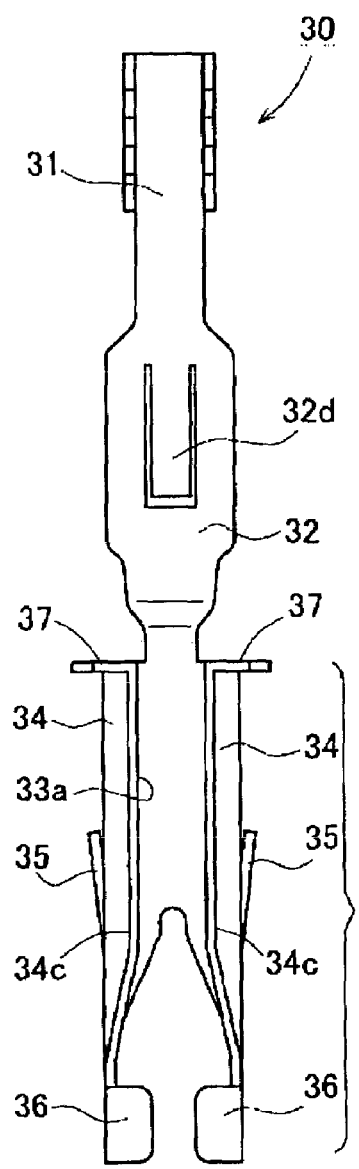
Figure 3:
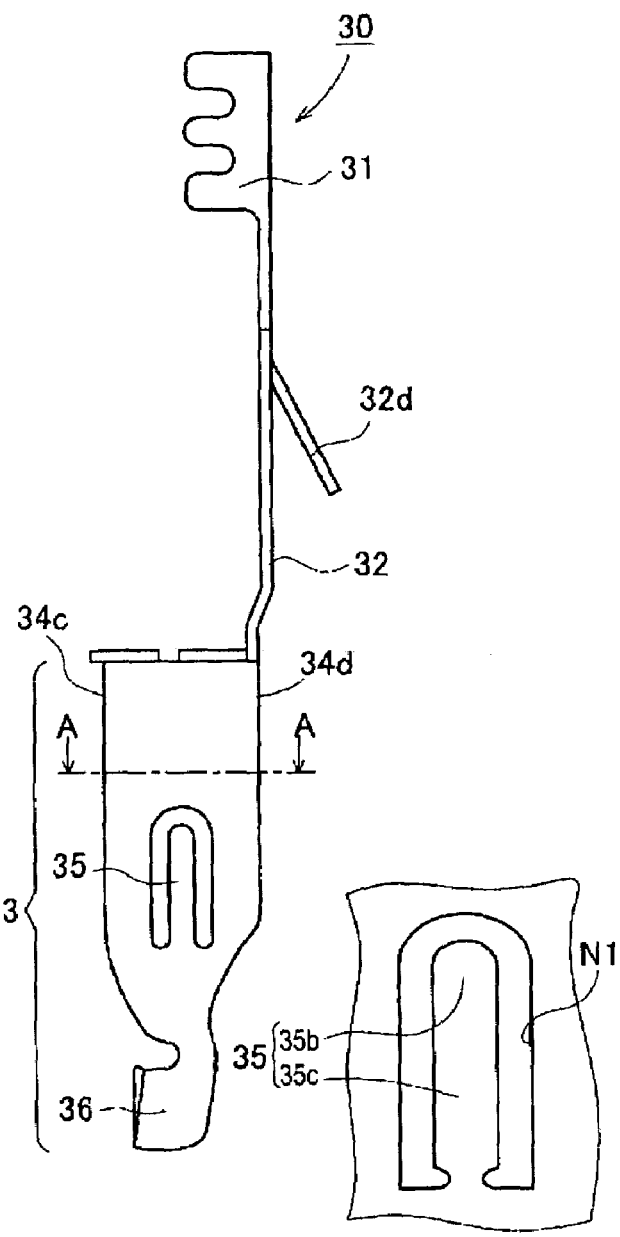

As shown in FIG. 3, the terminal member 30, which is formed of a single metal plate (stainless steel plate in the present embodiment), has an insertion portion 33 and flange portions 37. The insertion portion 33 is bent such that it has a generally horseshoe-shaped cross section, taken perpendicular to the axis (hereinafter also referred to as "perpendicular cross section") and such that a slit 33a is formed (see FIG. 4). The flange portions 37 are continuously formed at the rear end (upper end in FIG. 3) of the insertion portion 33, and project radially outward. Further, the terminal member 30 has a separator insertion portion 32 extending toward the rear end side from a central portion of the rear end of the insertion portion 33, and a connector portion 31 located on the rear end side of the separator insertion portion 32. The connector portion 31 tightly holds a conductor of the sensor output lead wire 19 by means of crimping, to thereby electrically connect the terminal member 30 and the sensor output lead wire 19. The separator insertion portion 32 is inserted into the separator 18. As a result, a separator engagement portion 32d projectingly branched from the separator insertion portion 32 elastically engages the wall surface of a holding hole 18d, whereby the terminal member 30 is held in the separator 18. The insertion portion 33 is inserted into the bottomed hole 21 of the oxygen detection element 20, with the heater 12 being disposed in the insertion portion 33. The flange portions 37 come into contact with a rear end surface 26 of the oxygen detection element 20, whereby the insertion portion 33 positions the heater 12 within the oxygen detection element 20 along the direction of the axis AX.

Although not described in detail, a connection member 40 for the external electrode layer 25 is connected to the remaining sensor output lead wire 19b in the same manner as in the case of the terminal member 30. As shown in FIG. 1 and FIG. 2(a), the connection member 40 is fitted onto the oxygen detection element 20, and is electrically connected to the external electrode layer 25 via the terminal connection portion 27 and the connection lead portion 28.

As shown in FIG. 3, the insertion portion 33 includes an insertion body portion 34 and heater pressing portions 36 projecting from the insertion body portion 34 toward the tip end side (downward in FIG. 3). Each of the heater pressing portions 36 is formed in the shape of a quarter arc as viewed along the axial direction. When the insertion body portion 34 is assembled into the oxygen detection element 20, the heater pressing portions 36 press the heater 12 such that a side surface of the heater 12, held within the insertion body portion 34, comes into contact with the inner circumferential surface 22 of the oxygen detection element 20.

Also, as shown in FIG. 3, the insertion body portion 34 has contact portions 35 each formed at an axial position offset toward the tip end side (downward in FIG. 3). The contact portions 35 are each formed by punching an opening N1 having the shape of an inverted U (see the expanded portion of FIG. 3(b)). Each contact portion 35 assumes the shape of a cantilevered flat plate such that a rear-end-side portion (upper portion in expanded FIG. 3(b)) of each contact portion 35 serves as a free end, and each contact portion 35 is connected to the insertion body portion 34 via a tip-end-side portion (lower portion in expanded FIG. 3(b)) thereof. As shown in FIG. 3(a), the contact portions 35 are formed such that their free-end-side portions are bent slightly outward (leftward and rightward, respectively in FIG. 3(a)) so as to project from the insertion body portion 34. The free-end-side portions serve as conduction portions 35b for electrical connection with the internal electrode layer 23 of the oxygen detection element 20. The tip-end-side portions, which extend from the conduction portions 35b toward the tip end side (downward in expanded FIG. 3(b)), serve as tip-end-side continuous portions 35c.

Figure 4:
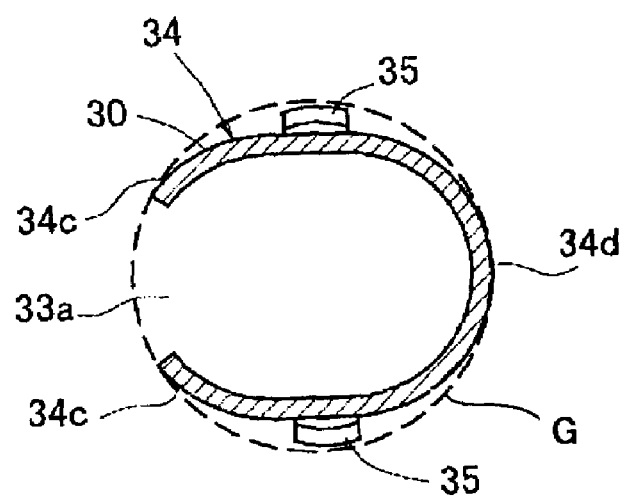
FIG. 4 is an explanatory sectional view taken along line A-A of FIG. 3(b) as viewed from the upper side (rear end side).

Moreover, as shown in FIG. 4, the insertion body portion 34 having a generally horseshoe-shaped perpendicular cross section has end press contact portions 34c at the circumferentially opposite ends in the cross section (more specifically, the opposite ends which define the slit 33a therebetween), and a central press contact portion 34d at the circumferentially central portion therebetween. Notably, FIG. 4 is an explanatory view showing a cross section of the terminal member 30 taken along line A-A of FIG. 3(b) and viewed from the upper side (rear end side).

In a free state before insertion, as indicated by a broken line in FIG. 4, the diameter of the circumcircle G is greater than the diameter of the bottomed hole 21 of the oxygen detection element 20.

Figures 5A, 5B:
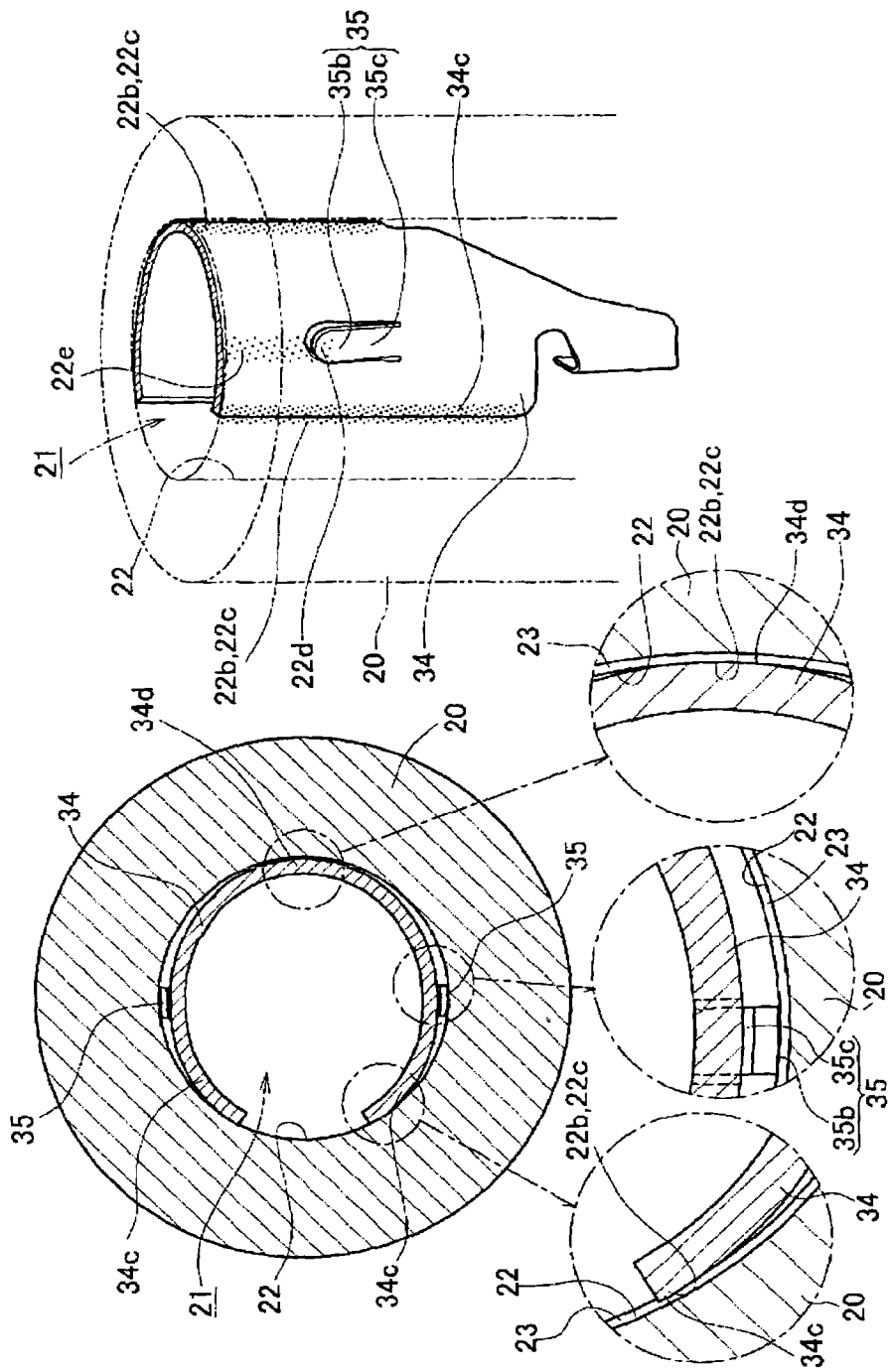

As shown in FIGS. 5(a) and 5(b), in a state in which the insertion body portion 34 is inserted into the bottomed hole 21 of the oxygen detection element 20, the diameter G of the circumcircle G of the insertion body portion 34 having a generally horseshoe-shaped perpendicular cross section is reduced. By means of elastic restoration force of the insertion body portion 34, the end press contact portions 34c and the central press contact portion 34d press the inner circumferential surface 22 of the oxygen detection element 20. Accordingly, by adjusting the degree of bending, dimensions, etc., of the insertion body portion 34, the terminal member 30 itself comes into pressure contact with the wall surface of the bottomed hole 21 with a suitable, relatively large pressing force per unit area, via the end press contact portions 34c and the central press contact portion 34d.

Meanwhile, by adjusting the degree of bending, dimensions, etc., of the tip-end-side continuous portions 35c performed in consideration of the strength of the internal electrode layer 23, the conduction portions 35b come into pressure contact with the wall surface of the bottomed hole 21 with a proper, relatively small pressing force per unit area which is suitable for establishing electrical continuity with the internal electrode layer 23.

As described above, in the oxygen sensor 10 of the first embodiment, the terminal member 30 has not only the end press contact portions 34c and the central press contact portion 34d, which hold the terminal member 30 itself on the inner circumferential surface of the oxygen detection element 20, but also the conduction portions 35b for establishing electrical connection between the terminal member 30 and the internal electrode layer 23; and the pressing force produced at the conduction portions 35b is made smaller than that produced at the end press contact portions 34c and the central press contact portion 34d.

Accordingly, the oxygen sensor 10 is highly reliable in terms of both holding the terminal member 30 and establishing electrical conductivity.

In the first embodiment, the internal electrode layer 23 of the oxygen detection element 20 is formed over the entire circumference of the inner circumferential surface 22. As described below, when the insertion portion 33 of the terminal member 30 is inserted into the oxygen detection element 20, in some cases the end press contact portions 34c and the central press contact portion 34d scrape the internal electrode layer 23. However, even when the internal electrode layer 23 is scraped because of sliding movement of the end press contact portions 34c and the central press contact portion 34d of the terminal member 30, the internal electrode layer 23 is not necessarily removed completely at portions (press-contact-portion sliding regions 22c described below) where the end press contact portions 34c, etc., have slid. In the first embodiment, even at portions of the internal electrode layer 23 where the end press contact portions 34c, etc. have slid, the inner circumferential surface of the oxygen detection element 20 is not exposed, despite a decrease in the thickness of the internal electrode layer 23. Therefore, in the first embodiment, the end press contact portions 34c and the central press contact portion 34d also come into contact with the internal electrode layer 23. Since this configuration establishes electrical continuity with the internal electrode layer 23 not only by means of the conduction portions 35b of the terminal member 30 but also by means of the end press contact portions 34c and the central press contact portion 34d, the reliability of the oxygen sensor 10 can be improved further.

Next, manufacture of the oxygen sensor 10 according to the first embodiment will be described. Since known methods can be employed for manufacturing the oxygen sensor 10 except for assembly of the terminal member 30 into the oxygen detection element 20, only a process for assembling the terminal member 30 into the oxygen detection element 20 will be described.

Figure 6:
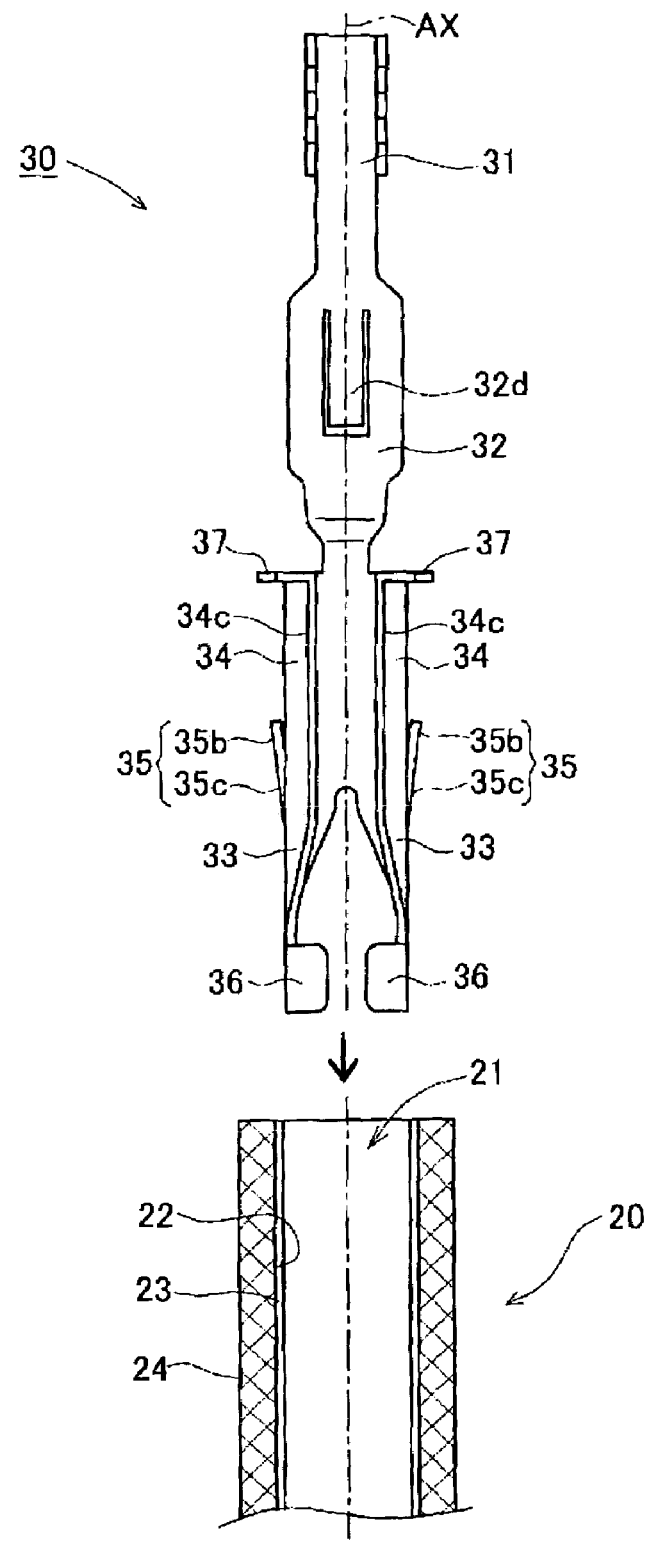
FIG. 6 is an explanatory view showing assembly of the terminal member according to the first embodiment into an oxygen detection element.

The insertion body portion 34 and the heater press portions 36 of the terminal member 30 are inserted into the bottomed hole 21 of the oxygen detection element 20 as shown in FIG. 6, whereby the terminal member 30 is assembled into the oxygen detection element 20. The insertion operation is performed in such a manner that, in a state in which the end press contact portions 34c and the central press contact portion 34d of the insertion body portion 34 are in press contact with the inner circumferential surface 22 of the oxygen detection element 20, the terminal member 30 is slid along the direction of the axis AX toward the tip end side. At this time, as a result of insertion of the insertion body portion 34, the end press contact portions 34c and the central press contact portion 34d slide on the inner circumferential surface 22 of the oxygen detection element 20 in a strongly pressed state. In the oxygen sensor 10 of the first embodiment, the internal electrode layer 23 is formed over the entire circumference of the inner circumferential surface 22 of the oxygen detection element 20. Therefore, portions of the internal electrode layer 23 contained in the press-contact-portion sliding regions 22c (see FIG. 5(b)); i.e., regions in which the end press contact portions 34c and the central press contact portion 34d have slid, may be scraped or exfoliated to some degree because of the sliding movement.

In the oxygen sensor 10 of the first embodiment, the end press contact portions 34c and the central press contact portion 34d axially extend to reach the flange portions 37. Therefore, press contact regions 22b of the inner circumferential surface 22 of the oxygen detection element 20; i.e., regions where the end press contact portions 34c and the central press contact portion 34d are in pressure contact with the inner circumferential surface 22, completely overlap the press-contact-portion sliding regions 22c.

Meanwhile, the conduction portions 35b are in contact with the internal electrode layer 23 in conduction-portion contact regions 22d of the inner circumferential surface 22 of the oxygen detection element 20, which regions are circumferentially shifted from the press contact regions 22b and the press-contact-portion sliding regions 22c. That is, the conduction portions 35b are in contact with portions of the internal electrode layer 23 where the end press contact portions 34c and the central press contact portion 34d of the terminal member 30 have not slid, and the internal electrode layer 23 is not scraped or exfoliated. Accordingly, in the conduction-portion contact regions 22d, electrical continuity can be reliably established between the conduction portions 35b and the internal electrode layer 23. In addition, the pressing force per unit area that the conduction portions 35b exert on the inner circumferential surface 22 is small as compared with that exerted by the end press contact portions 34c, etc. Therefore, in conduction-portion sliding regions 22e of the inner circumferential surface 22, in which the conduction portions 35b have slid, the internal electrode layer 23 is hardly scraped or exfoliated.

Notably, each of the contact portions 35 of the terminal member 30 has a tip-end-side continuous portion 35c located on the tip end side of the conduction portion 35b. Tip-end-side continuous portion 35c does not come into contact with the inner surface of the oxygen detection element 20, and conduction portion 35b extends from 35c. Accordingly, when the insertion body portion 34 of the terminal member 30 is inserted into the bottomed hole 21 of the oxygen detection element 20, prior to the conduction portions 35b, the tip-end-side continuous portions 35c are inserted without coming into contact with the inner surface (the internal electrode layer 23) of the oxygen detection element 20. After that, the conduction portions 35b are inserted while being guided by the tip-end-side continuous portions 35c. Therefore, the conduction portions 35b can be smoothly inserted to correct positions on the rear end side of the tip-end-side continuous portions 35c. Accordingly, the oxygen sensor 10 can be manufactured in such manner that the conduction portions 35b are disposed at correct positions and press the inner circumferential surface 22 of the oxygen detection element 20 with a suitable pressing force per unit area to thereby establish continuity with the internal electrode layer 23.

First Modification

Figure 7:
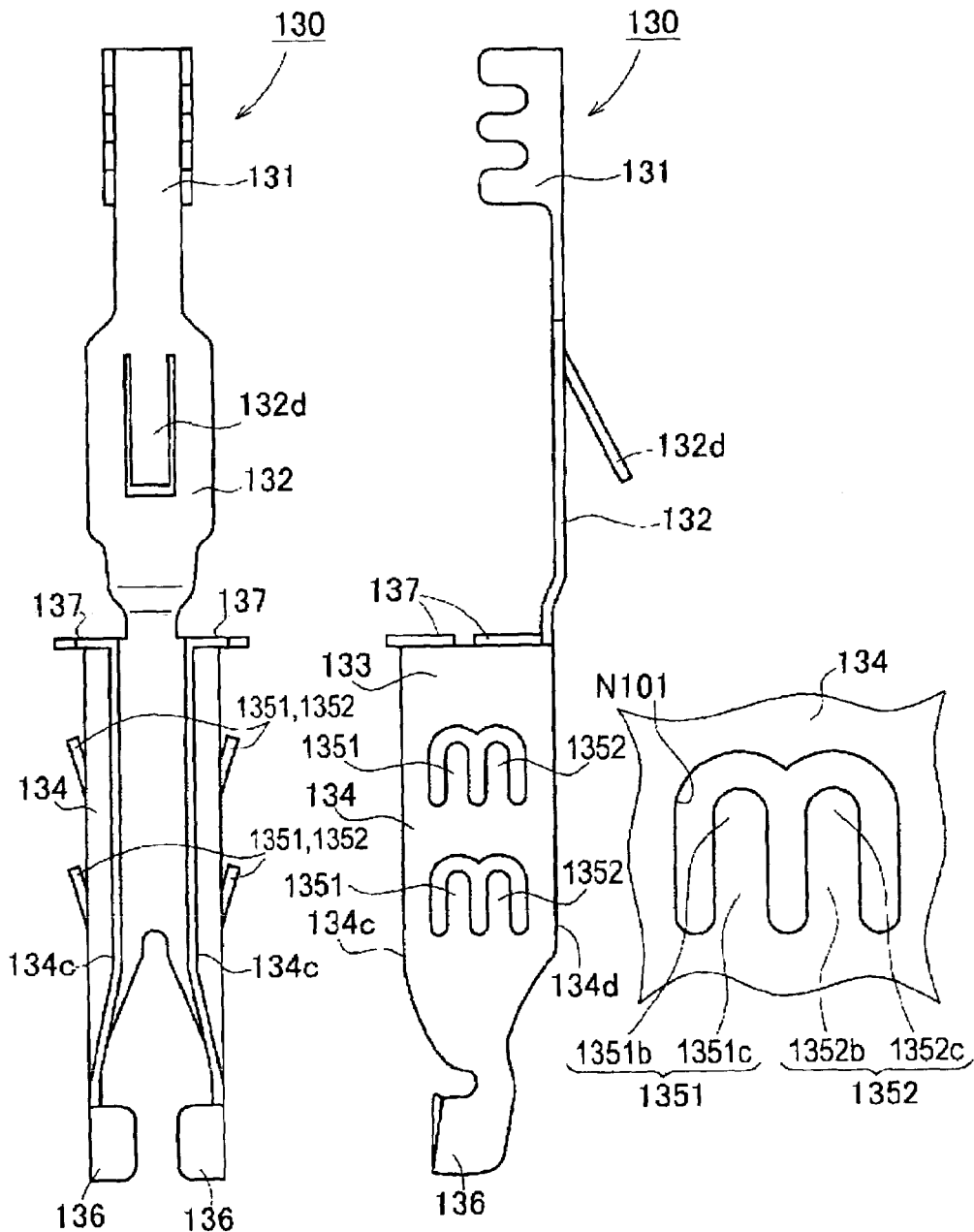

Next, an oxygen sensor 110 according to a first modification will be described with reference to FIGS. 1 and 7. The oxygen sensor 110 according to the first modification differs from the oxygen sensor 10 of the first embodiment in that the terminal member 30 is replaced with a terminal member 130. Therefore, portions of the terminal member 130 which differ from those of the terminal member 30 will be mainly described, and descriptions of the similar portions will be omitted or simplified.

A connector portion 131, a separator insertion portion 132, a separator engagement portion 132d, heater pressing portions 136, and flange portions 137 of the terminal member 130 are identical to the connector portion 31, the separator insertion portion 32, the separator engagement portion 32d, the heater pressing portions 36, and the flange portions 37 of the first embodiment. However, an insertion body portion 134 of an insertion portion 133 of the terminal member 130 has contact portions 1351 and 1352, which differ in shape from the contact portions 35 of the first embodiment. That is, as shown in FIG. 7, in the terminal member 130, paired contact portions 1351 and 1352 are provided at each of an axial position offset toward the tip end side (downward in FIG. 7) and an axial position offset toward the rear end side (upward in FIG. 7), whereby four contact portions are provided in total. The contact portions 1351 and 1352 are formed by punching an opening N101 having the shape of an inverted W.

As in the case of the contact portions 35, each of the contact portions 1351 and 1352 assumes the shape of a cantilevered flat plate such that a rear-end-side portion (upper portion in FIG. 7) serves as a free end, and each contact portion is connected to the insertion body portion 134 via a tip-end-side portion (lower portion in FIG. 7) thereof. Moreover, the contact portions 1351 and 1352 are formed such that their free-end-side portions are bent slightly outward so as to project from the insertion body portion 134.

As in the case of the contact portions 35, the free-end-side portions of the contact portions 1351 and 1352 serve as conduction portions 1351b and 1352b for electrical connection with the internal electrode layer 23; and the portions which extend from these conduction portions toward the tip end side serve as tip-end-side continuous portions 1351c and 1352c. Through adjustment of dimensions, bent angle, etc., of the tip-end-side continuous portions 1351c and 1352c, in a state in which the terminal member 130 is assembled into the oxygen detection element 20, the conduction portions 1351b and 1352b come into pressure contact with the internal electrode layer 23 with a proper, relatively small pressing force per unit area which is suitable for establishing electrical continuity with the internal electrode layer 23 in consideration of the strength of the internal electrode layer 23.

The oxygen sensor 110 of the first modification has four sets of the contact portions 1351 and 1352, which function in the same manner as the contact portions 35 of the first embodiment. Therefore, the terminal member 130 comes into contact with the internal electrode layer 23 of the oxygen detection element 20 via the eight conduction portions 1351b and 1352b. More reliable electrical continuity can be established between the internal electrode layer 23 and the terminal member 130. Accordingly, the oxygen sensor 110 of the first modification has a higher reliability.

Second Modification

Next, an oxygen sensor 210 according to a second modification will be described with reference to FIGS. 1 and 8. The oxygen sensor 210 according to the second modification differs from the oxygen sensor 10 of the first embodiment in that the terminal member 30 is replaced with a terminal member 230. Therefore, portions of the terminal member 230 which differ from those of the terminal member 30 will be mainly described, and descriptions of the similar portions will be omitted or simplified.

A connector portion 231, a separator insertion portion 232, a separator engagement portion 232d, heater pressing portions 236, and flange portions 237 of the terminal member 230 are identical to the connector portion 31, the separator insertion portion 32, the separator engagement portion 32d, the heater pressing portions 36, and the flange portions 37 of the first embodiment. However, as shown in FIG. 8, the terminal member 230 differs from the terminal member 30 of the first embodiment in that the terminal member 230 has a contact portion 235 which projects toward the tip end side (downward in FIG. 8) from a tip-end-side portion of a circumferentially central portion of an insertion body portion 234 of an insertion portion 233.

As shown in FIG. 8, the terminal member 230 has a contact portion 235 which extends toward the tip end side from a tip-end-side portion of the insertion body portion 234 at a circumferentially central position as viewed in a generally horseshoe-shaped perpendicular cross section. The contact portion 235 assumes an angularly bent shape such that a tip-end-side portion (lower portion in FIG. 8) serves as a free end, and the contact portion is connected to the insertion body portion 234 via a rear-end-side portion (upper portion in FIG. 8) thereof.

A bent portion of the contact portion 235 located outermost in the radial direction serves as a conduction portion 235b for electrical connection with the internal electrode layer 23 of the oxygen detection element 20; and a continuous portion 235c is provided to extend between the conduction portion 235b and the insertion body portion 234. Through adjustment of dimensions, etc., of the continuous portion 235c, the conduction portion 235b comes into pressure contact with the internal electrode layer 23 with a proper, relatively small pressing force per unit area which is suitable for establishing electrical continuity with the internal electrode layer 23 in consideration of the strength of the internal electrode layer 23.

In the oxygen sensor 210 of the second modification, the terminal member 230 has a conduction portion 235b for establishing electrical connection between the terminal member 230 and the internal electrode layer 23, separately from end press contact portions 234c and a central press contact portion 234d for holding the terminal member 230 itself on the inner circumferential surface 22 of the oxygen detection element 20.

Accordingly, since the terminal member 230 comes into contact with the inner circumferential surface 22 with a pressing force per unit area suitable for holding and for establishing electrical continuity, the oxygen sensor 210 is reliable in terms of holding of the terminal member 230 and establishing electrical continuity.

Notably, in the second modification, since contact for electrical connection is established between the internal electrode layer 23 and the end press contact portions 234c and the central press contact portion 234d, the reliability can be improved further.

Third Modification

Figure 9:
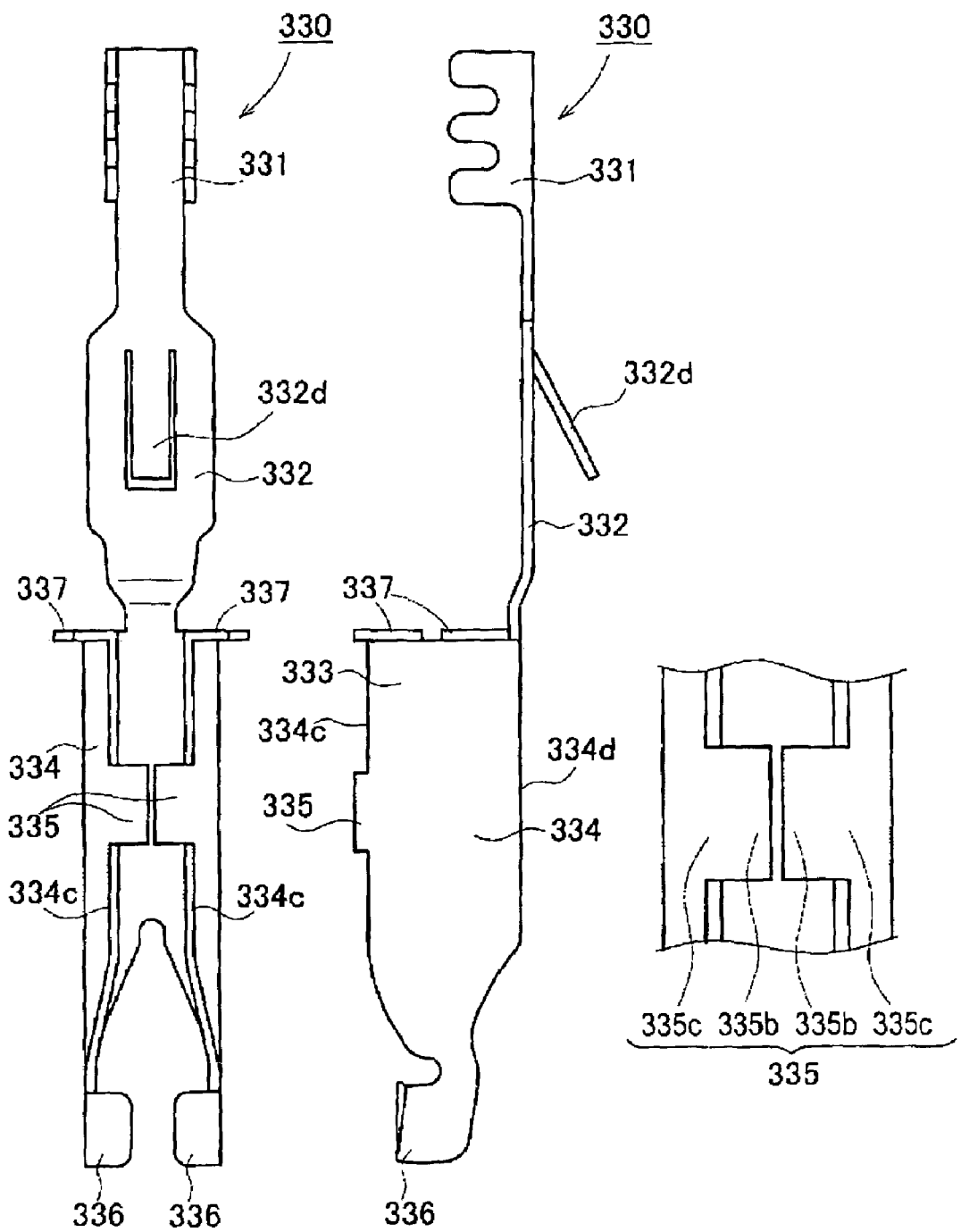

Next, an oxygen sensor 310 according to a third modification will be described with reference to FIGS. 1 and 9. The oxygen sensor 310 according to the third modification differs from the oxygen sensor 10 of the first embodiment in that the terminal member 30 is replaced with a terminal member 330.

Therefore, portions of the terminal member 330 which differ from those of the terminal member 30 will be mainly described, and descriptions of the similar portions will be omitted or simplified.

A connector portion 331, a separator insertion portion 332, a separator engagement portion 332d, heater pressing portions 336, and flange portions 337 of the terminal member 330 are identical to the connector portion 31, the separator insertion portion 32, the separator engagement portion 32d, the heater pressing portions 36, and the flange portions 37 of the first embodiment. However, as shown in FIG. 9, the terminal member 330 differs from the terminal member 30 of the first embodiment in that the terminal member 330 has contact portions 335 which circumferentially extend from the circumferential ends of an insertion body portion 334 of an insertion portion 333 as viewed in the perpendicular cross section thereof. Each of the contact portions 335 has a conduction portion 335b which is located at a tip end in the circumferential direction and which comes into contact with the internal electrode layer 23 of the oxygen detection element 20 to thereby establish electrical continuity therewith, and a continuous portion 335c which extends between the conduction portions 335b and the insertion body portion 334 and urges the contact portion 335 such that the conduction portion 335b comes into pressure contact with the internal electrode layer 23 with a suitable pressing force per unit area.

In the oxygen sensor 310 of the third modification, the terminal member 330 has conduction portions 335b for establishing electrical connection between the terminal member 330 and the internal electrode layer 23, separately from end press contact portions 334c and a central press contact portion 334d for holding the terminal member 330 itself on the inner circumferential surface 22 of the oxygen detection element 20.

Accordingly, since press contact for holding and press contact for electrical continuity can be suitably attained, the oxygen sensor 310 is reliable in terms of holding of the terminal member 330 and establishing electrical continuity.

Notably, in the third modification, since contact for electrical connection is established between the internal electrode layer 23 and the end press contact portions 334c and the central press contact portion 334d, reliability can be improved further.

Second Embodiment

Figure 10:
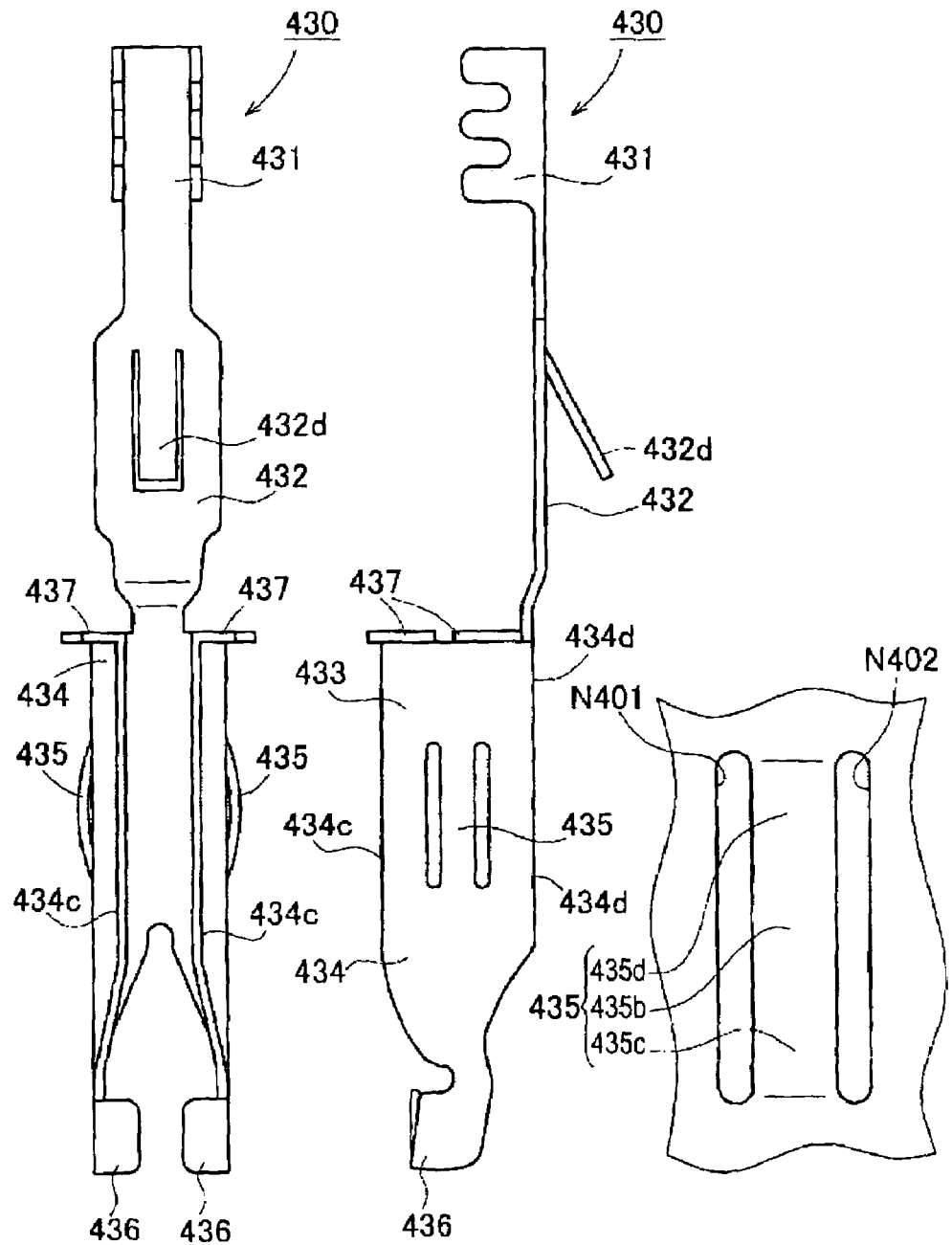

Next, an oxygen sensor 410 according to a second embodiment will be described with reference to FIGS. 1 and 10. The oxygen sensor 410 according to the second embodiment differs from the oxygen sensor 10 of the first embodiment in that the terminal member 30 is replaced with a terminal member 430. Therefore, portions of the terminal member 430 which differ from those of the terminal member 30 will be mainly described, and descriptions of similar portions will be omitted or simplified.

A connector portion 431, a separator insertion portion 432, a separator engagement portion 432d, heater pressing portions 436, and flange portions 437 of the terminal member 430 are identical to the connector portion 31, the separator insertion portion 32, the separator engagement portion 32d, the heater pressing portions 36, and the flange portions 37 of the first embodiment. However, in contrast to the first embodiment in which the contact portions 35 are cantilevered, in the second embodiment, contact portions 435 are supported at opposite ends. Specifically, in the second embodiment, the contact portions 435 are provided on an insertion body portion 434 at generally central locations in the axial direction, as shown in FIG. 10. Each of the contact portions 435 is formed by punching openings N401 and N402 in the insertion body portion 434 parallel to the axial direction, so that a portion between the openings N401 and N402 bulges outward. Each contact portion 435 is connected to the insertion body portion 434 at a tip-end-side end (lower end in FIG. 10) and a rear-end-side end (upper end in FIG. 10) thereof, so that each contact portion 435 assumes the shape of an outwardly curved plate. A central portion of each contact portion 435 serves as a conduction portion 435b which comes into contact with the internal electrode layer 23 of the oxygen detection element 20 to thereby establish electrical continuity therewith. A tip-end-side continuous portion 435c extends continuously from the central portion toward the tip end side (lower side in FIG. 10), and a rear-end-side continuous portion 435d extends continuously from the central portion toward the rear end side (upper side in FIG. 10). Through adjustment of dimensions, etc., of the tip-end-side continuous portion 435c and the rear-end-side continuous portion 435d performed in consideration of the strength of the internal electrode layer 23, the conduction portion 435b comes into pressure contact with the internal electrode layer 23 with a proper, relatively small pressing force per unit area which is suitable for establishing electrical continuity with the internal electrode layer 23.

In the oxygen sensor 410 of the second embodiment, the terminal member 430 has conduction portions 435b for establishing electrical connection between the terminal member 430 and the internal electrode layer 23, separately from end press contact portions 434c and a central press contact portion 434d for holding the terminal member 430 itself on the inner circumferential surface 22 of the oxygen detection element 20.

Accordingly, the oxygen sensor 410 is reliable in terms of holding of the terminal member 430 and establishing electrical continuity.

Notably, in the second embodiment, since contact for electrical connection is established between the internal electrode layer 23 and the end press contact portions 434c and the central press contact portion 434d, the reliability can be improved further.

Moreover, in the oxygen sensor 410 of the second embodiment, the contact portions 435 of the terminal member 430 each have a tip-end-side continuous portion 435c from which the conduction portion 435b continuously extends. Accordingly, when the insertion body portion 434 of the terminal member 430 is inserted into the oxygen detection element 20, the tip-end-side continuous portions 435c are first inserted, and after that, the conduction portions 435b are inserted while being guided by the tip-end-side continuous portions 435c. Therefore, the conduction portions 435b can be smoothly inserted to assume correctly aligned positions. Accordingly, the oxygen sensor 410 can be manufactured such that the conduction portions 435b are disposed at correctly aligned positions and press the inner circumferential surface 22 of the oxygen detection element 20 with a suitable pressing force per unit area.

Further, in the oxygen sensor 410 of the second embodiment, the contact portions 435 of the terminal member 430 each have a rear-end-side continuous portion 435d as well. Therefore, the range of adjustment of pressing force of the conduction portions 435b can be widened as compared with terminal members which do not have the rear-end-side continuous portion, whereby adjustment is facilitated. Furthermore, in the oxygen sensor 410, since each of the contact portions 435 has both the tip-end-side continuous portion 435c and the rear-end-side continuous portion 435d continuous with the conduction portion 435b, resonance is less likely as compared with the case where each conduction portion has the tip-end-side continuous portion or the rear-end-side continuous portion only. Accordingly, since pressing force is less likely to change because of vibration, the oxygen sensor 410 is a gas sensor of higher reliability in terms of electrical continuity under vibration.

Fourth Modification

Figure 11:
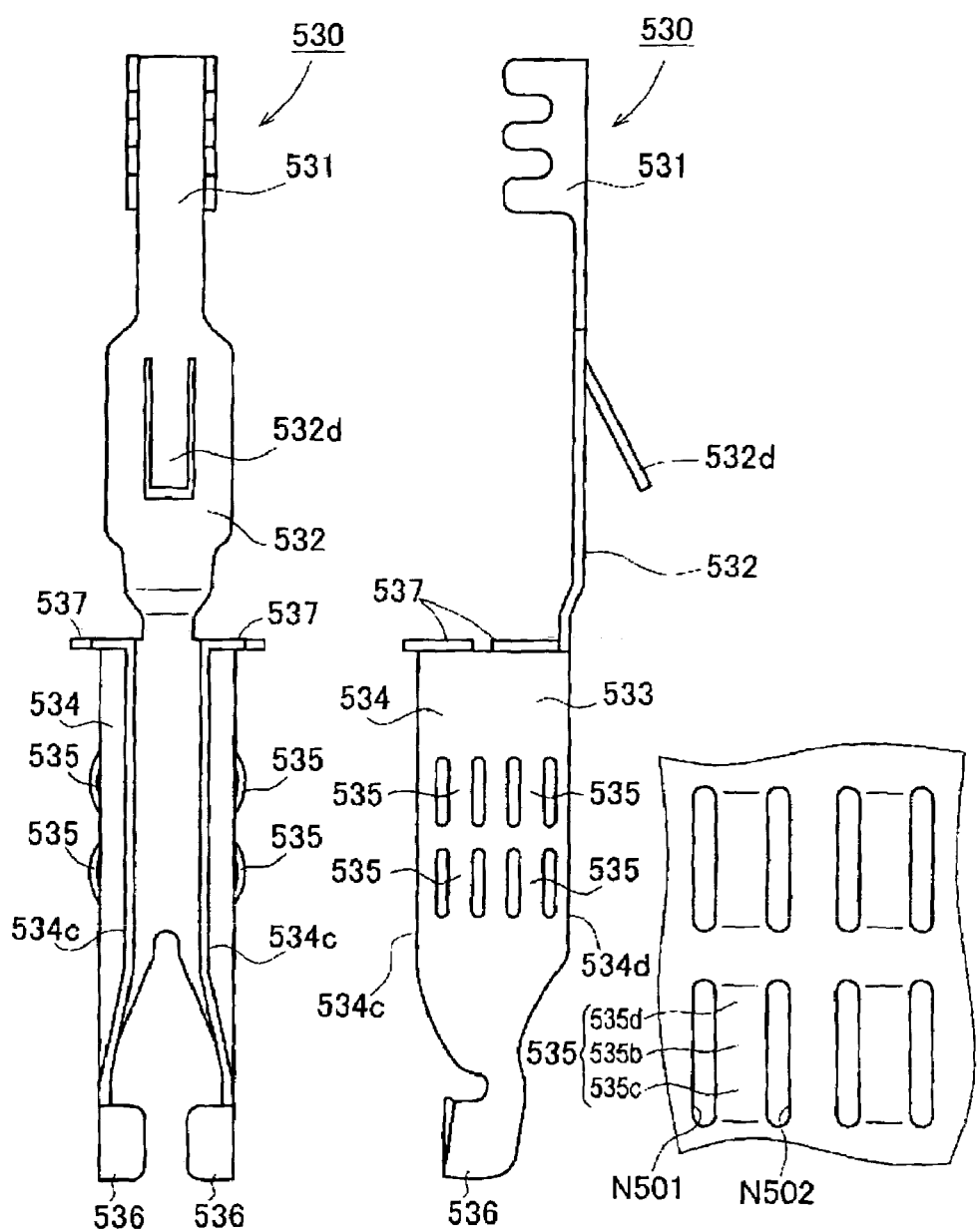

Next, an oxygen sensor 510 according to a fifth modification will be described with reference to FIGS. 1 and 11. The oxygen sensor 510 according to the fourth modification differs from the oxygen sensor 10 of the first embodiment in that the terminal member 30 is replaced with a terminal member 530. Therefore, portions of the terminal member 530 which differ from those of the terminal member 30 will be mainly described, and descriptions of the similar portions will be omitted or simplified.

A connector portion 531, a separator insertion portion 532, a separator engagement portion 532d, heater pressing portions 536, and flange portions 537 of the terminal member 530 are identical to the connector portion 31, the separator insertion portion 32, the separator engagement portion 32d, the heater pressing portions 36, and the flange portions 37 of the first embodiment. However, as shown in FIG. 11, the terminal member 530 of the fourth modification has eight contact portions 535 which are similar to the contact portions 435 of the above-described second embodiment, each of which has a tip-end-side continuous portion 535c and a rear-end-side continuous portion 535d.

Accordingly, in the oxygen sensor 510 of the fourth modification, more reliable electrical continuity can be established between conduction portions 535b and the internal electrode layer 23 as compared with the oxygen sensor 410 of the second embodiment. Therefore, the reliability of the oxygen sensor 510 can be improved further.

The present invention has been described in accordance with the above first and second embodiments and first through fourth modifications. Needless to say, the present invention is not limited to these embodiments and modifications, and may be practiced in a modified form without departing from the scope of the invention.

For example, in the embodiments and modifications, oxygen sensors are described as example gas sensors. However, the present invention can be applied to other types of gas sensors such as a NOx sensor, a CO sensor, a HC sensor, in which the materials of the external electrode layer 25 and/or the internal electrode layer 23 are adjusted such that the output changes with the concentration of a gas such as NOx, CO, HC, or the like.

In the first and fourth modifications, four contact portions are provided on each side. However, a larger number of (e.g., six) contact portions or a smaller number of (e.g., three) contact portions may be provided.

The embodiments and modifications exemplify the case where the heater 12 is disposed within the terminal member. However, the present invention can be applied to gas sensors which do not have a heater.

This application is based on Japanese Patent Application No. 2004-106905 filed Mar. 31, 2004, incorporated herein by reference in its entirety.

What is claimed is:
1. A gas sensor comprising:
a gas detection element in the form of a hollow tube having a closed tip end and an opened rear end and extending along an axis and which has an electrode layer formed on at least a portion of an inner circumferential surface of the gas detection element; and a terminal member contacting the electrode layer and electrically connected therewith, wherein the terminal member includes a press contact portion which comes into press contact with the inner circumferential surface of the gas detection element to hold the terminal member in the gas detection element, and a conduction portion which comes into press contact with the electrode layer on the inner circumferential surface of the gas detection element and into electrical connection with the electrode layer, and wherein a pressing force per unit area at the conduction portion is smaller than a pressing force per unit area at the press contact portion, and wherein the conduction portion is separated from the press contact portion.

2. The gas sensor as claimed in claim 1, wherein the conduction portion of the terminal member comes into contact with the electrode layer and into electrical connection therewith in a region of the inner circumferential surface of the gas detection element other than a press contact region where the press contact portion is in press contact with the inner circumferential surface and other than a press-contact-portion sliding region in which the press contact portion has slid.

3. The gas sensor as claimed in claim 1, wherein the press contact portion also comes into contact with the electrode layer and into electrical connection therewith.

4. The gas sensor as claimed in claim 2, wherein the press contact portion also comes into contact with the electrode layer and into electrical connection therewith.

5. The gas sensor as claimed in claim 1, wherein the terminal member includes a tip-end-side continuous portion which extends from the conduction portion toward the tip end side without coming into contact with the inner circumferential surface of the gas sensor element; and the tip-end-side continuous portion presses the conduction portion toward the inner circumferential surface of the gas detection element by elastic deformation of the tip-end-side continuous portion.

6. The gas sensor as claimed in claim 2, wherein the terminal member includes a tip-end-side continuous portion which extends from the conduction portion toward the tip end side without coming into contact with the inner circumferential surface of the gas sensor element; and the tip-end-side continuous portion presses the conduction portion toward the inner circumferential surface of the gas detection element by elastic deformation of the tip-end-side continuous portion.

7. The gas sensor as claimed in claim 3, wherein the terminal member includes a tip-end-side continuous portion which extends from the conduction portion toward the tip end side without coming into contact with the inner circumferential surface of the gas sensor element; and the tip-end-side continuous portion presses the conduction portion toward the inner circumferential surface of the gas detection element by elastic deformation of the tip-end-side continuous portion.

8. The gas sensor as claimed in claim 1, wherein the terminal portion includes:

a tip-end-side continuous portion which extends from the conduction portion toward the tip end side without coming into contact with the inner circumferential surface of the gas sensor element, and a rear-end-side continuous portion which extends from the conduction portion toward the rear end side without coming into contact with the inner circumferential surface of the gas sensor element, wherein the tip-end-side continuous portion and the rear-end-side continuous portion press the conduction portion toward the inner circumferential surface of the gas detection element by elastic deformation of the tip-end-side continuous portion and the rear-end-side continuous portion.

9. The gas sensor as claimed in claim 2, wherein the terminal portion includes:

a tip-end-side continuous portion which extends from the conduction portion toward the tip end side without coming into contact with the inner circumferential surface of the gas sensor element, and a rear-end-side continuous portion which extends from the conduction portion toward the rear end side without coming into contact with the inner circumferential surface of the gas sensor element, wherein the tip-end-side continuous portion and the rear-end-side continuous portion press the conduction portion toward the inner circumferential surface of the gas detection element by elastic deformation of the tip-end-side continuous portion and the rear-end-side continuous portion.

10. The gas sensor as claimed in claim 3, wherein the terminal portion includes:

a tip-end-side continuous portion which extends from the conduction portion toward the tip end side without coming into contact with the inner circumferential surface of the gas sensor element, and a rear-end-side continuous portion which extends from the conduction portion toward the rear end side without coming into contact with the inner circumferential surface of the gas sensor element, wherein the tip-end-side continuous portion and the rear-end-side continuous portion press the conduction portion toward the inner circumferential surface of the gas detection element by elastic deformation of the tip-end-side continuous portion and the rear-end-side continuous portion.

11. The gas sensor as claimed in claim 1, wherein the terminal member holds itself in the gas detection element by means of the press contact portion.

12. A gas sensor comprising a gas detection element in the form of a hollow tube having a closed tip end and an opened rear end and extending along an axis and which has an electrode layer formed on at least a portion of an inner circumferential surface of the gas detection element; and a terminal member contacting the electrode layer and electrically connected therewith, wherein the terminal member includes a press contact portion which comes into press contact with the inner circumferential surface of the gas detection element to hold the terminal member in the gas detection element, and a conduction portion which comes into press contact with the electrode layer on the inner circumferential surface of the gas detection element and into electrical connection with the electrode layer, wherein a pressing force per unit area at the conduction portion is smaller than a pressing force per unit area at the press contact portion, and wherein the conduction portion of the terminal member comes into contact with the electrode layer and into electrical connection therewith in a region of the inner circumferential surface of the gas detection element other than a press contact region where the press contact portion is in press contact with the inner circumferential surface and other than a press-contact-portion sliding region, said sliding region being located on a rear end side of the press contact region and in which the press contact portion has slid.

13. The gas sensor as claimed in claim 12, wherein the conduction portion is separated from the press contact portion.

* * * * *